US010975353B2

(12) United States Patent
Geyer et al.

(10) Patent No.: US 10,975,353 B2
(45) Date of Patent: Apr. 13, 2021

(54) CULTURE MEDIUM FOR CELLULAR IMMUNOTHERAPY

(71) Applicant: polybiocept GmbH, Alzenau (DE)

(72) Inventors: Jakob Geyer, Osterholz-Scharmbeck (DE); Markus Maeurer, Äkersberga (SE); Ernest Dodoo, Stockholm (SE)

(73) Assignee: polybiocept GmbH, Alzenau (DE)

( * ) Notice: Subject to any disclaimer, the term of this patent is extended or adjusted under 35 U.S.C. 154(b) by 154 days.

(21) Appl. No.: 15/317,774

(22) PCT Filed: Jun. 10, 2015

(86) PCT No.: PCT/EP2015/062992
§ 371 (c)(1),
(2) Date: Dec. 9, 2016

(87) PCT Pub. No.: WO2015/189301
PCT Pub. Date: Dec. 17, 2015

(65) Prior Publication Data
US 2017/0121680 A1 May 4, 2017

(30) Foreign Application Priority Data

Jun. 10, 2014 (DE) .................... 10 2014 211 052.1

(51) Int. Cl.
| *C12N 5/078* | (2010.01) |
| *C12N 5/0786* | (2010.01) |
| *C12N 5/0787* | (2010.01) |
| *C12N 5/0783* | (2010.01) |

(52) U.S. Cl.
CPC ......... *C12N 5/0634* (2013.01); *C12N 5/0636* (2013.01); *C12N 5/0642* (2013.01); *C12N 5/0645* (2013.01); *C12N 2500/32* (2013.01); *C12N 2500/34* (2013.01); *C12N 2500/36* (2013.01); *C12N 2501/105* (2013.01); *C12N 2501/11* (2013.01); *C12N 2501/115* (2013.01); *C12N 2501/135* (2013.01); *C12N 2501/20* (2013.01); *C12N 2501/2302* (2013.01); *C12N 2501/2306* (2013.01); *C12N 2501/2315* (2013.01); *C12N 2501/2321* (2013.01); *C12N 2501/25* (2013.01); *C12N 2501/33* (2013.01); *C12N 2501/375* (2013.01); *C12N 2501/39* (2013.01); *C12N 2501/392* (2013.01); *C12N 2501/998* (2013.01)

(58) Field of Classification Search
None
See application file for complete search history.

(56) References Cited

U.S. PATENT DOCUMENTS 5,648,350 A * 7/1997 De Lignieres ....... A61K 31/568
514/178
2001/0028878 A1 10/2001 Lindenberg et al.
2002/0115211 A1 8/2002 Lindenberg et al.
2009/0017539 A1 1/2009 Spanholtz
2009/0221077 A1 9/2009 Ideno et al.

FOREIGN PATENT DOCUMENTS

| CN | 1839202 | 9/2006 |
| JP | 2001-275662 | 10/2001 |
| JP | 2002-519640 | 7/2002 |
| JP | 2003-235548 | 8/2003 |
| RU | 2 415 929 | 4/2011 |
| WO | 99/67365 | 12/1999 |
| WO | 2007/037682 | 4/2007 |

OTHER PUBLICATIONS

J.P. McNamee, P.V. Bellier, B.C. Kutzner, R.C. Wilkins, Effect of pro-inflammatory cytokines on spontaneous apoptosis in leukocyte sub-sets within a whole blood culture, 2005, Cytokine, vol. 31, pp. 161-167 (Year: 2005).*
International Committee for Standardization in Haematology (Dr J. Fielding, corresponding author), Recommendations for Measurement of Serum Iron in Human Blood,1978, British Journal of Haematology, vol. 38, pp. 291-294 (Year: 1978).*
BioVendor Product Catalog, accessed at http://www.tataa.com/wp-content/uploads/2012/10/BioVendor-Product-Catalogue-2014_2015.pdf on Nov. 29, 2019, online since Nov. 1, 2012 according to Google (see p. 1). (Year: 2012).*
Litvinova et al., "Influence of Immunoregulatory Cytokines (IL-2, IL-7 and IL-15), In Vitro Upon Activation, Proliferation and Apoptosis of Immune Memory T-Cells", Tsitologiya, vol. 55, No. 8, pp. 566-571, 2013, with English abstract.
McNamee et al., "Effect of pro-inflammatory cytokines on spontaneous apoptosis in leukocyte sub-sets within a whole blood culture", Cytokine, 31 (2): 161-167 (2005).
McFaul et al., "Hemoglobin stimulates the release of proinflammatmy cytokines from leukocytes in whole blood", Journal of Laboratory and Clinical Medicine, 135 (3): 263-269 (2000).
Biesecker et al., "Interleukin-6 is a component of human umbilical cord serum and stimulates hematopoiesis in embryonic stem cells in vitro", Experimental Hematology, 21(6): 774-778 (1993).

(Continued)

*Primary Examiner* — Renee Claytor
*Assistant Examiner* — Trent R Clarke
(74) *Attorney, Agent, or Firm* — Wenderoth, Lind & Ponack, L.L.P.

(57) ABSTRACT

The present invention provides a method for preparing a cell culture medium comprising a mixture of blood products from two or more donors, comprising the steps of: a) providing at least a first blood product from a first donor; b) measuring the concentration of at least one quality factor in the first blood product; c) comparing the measured concentration of a quality factor to a concentration range predefined for the quality factor; d) selecting the first blood product for the cell culture medium if the concentration measured for the quality factor is in the predefined range and optionally converting the first selected blood product into a first processed blood product or else unselecting the first blood product.

4 Claims, No Drawings

(56) References Cited

OTHER PUBLICATIONS

International Search Report and Written Opinion of the International Searching Authority, dated Aug. 20, 2015 in corresponding International Application No. PCT/EP2015/062992.
"Process" section of "Cell Culture Catalogue", Life Technologies Japan Ltd., 2012, 3 pages, with partial translation.
Li Xia et al., "Effects of estradiol on the differential regulation of activation in un-primed and primed mouse lymphoytes", Modern Immunology, vol. 25, No. 3, pp. 231-238, with English Abstract.
Abstract PH-P113, NK Cell (from Primary NK Cell Cultures) Mediated Killing of Multiple Myeloma Cells In vitro, "Abstracts of the 40th Annual Meeting of the European Group for Blood and Marrow Transplantation", Bone Marrow Transplantation, Mar. 28, 2014, 1 page.

\* cited by examiner

CULTURE MEDIUM FOR CELLULAR IMMUNOTHERAPY

FIELD OF THE INVENTION

The present invention relates to cell culture media with high quality standards, in particular for growth and expansion immune cells of and a method of preparation.

BACKGROUND OF THE INVENTION

One of the most promising advances for the treatment of cancer is a new therapeutic class called active cellular immunotherapy. Active immunotherapies, stimulate the patient's immune system with the intent of promoting an antigen specific anti-tumor effect using the body's own immune cells. For this the immune cells are cultured in-vitro to increase the number of cells and influence the differentiation.

For culturing cells in-vitro several basic environmental requirements have to be met such as controlled temperature, substrate for cell attachment, and appropriate growth medium and incubator that maintains correct pH and osmolality.

Cell culture media formulations have been well documented in the literature and a number of media are commercially available. Cell culture media generally comprise an appropriate source of energy and compounds which regulate the cell cycle. A typical culture medium is composed of a complement of amino acids, vitamins, inorganic salts, glucose, and serum as a source of growth factors, hormones, and attachment factors. In addition to nutrients, the medium also helps maintain pH and osmolality.

Cell culture media formulations have been well documented in the literature and a number of media are commercially available. For cultivation and expansion of immune cells, in particular lymphocytes, typically the cell culture medium is derived from serum or plasma as these provide an environment for the immune cells that is similar to the natural environment of the body.

However, the proliferation rate and activity of lymphocytes expanded in a culture medium of the state of the art is not yet sufficient. Moreover, predictable results regarding the quantity, quality and viability of the lymphocyte expansion results are so far rare and the necessity of testing several batches of serum in order to identify the required quality is common practice.

Accordingly, it an object of the present invention to overcome at least one of the disadvantages of the prior art.

SUMMARY OF THE INVENTION

The present invention is inter alia based on the finding that the quality of the used cell culture medium has a major influence on the outcome of an expansion process of the lymphocytes for cellular immunotherapy. In particular, the present inventors have defined a variety of quality factors that determine the quality of cell culture medium with respect to lymphocyte expansion. The inventors were able to determine quality factors such as estradiol, cortisol, IGF-1, insulin and SHBG have to be present in certain predefined concentrations. A cell culture medium fulfilling the criteria determined for the individual quality factors provides an improved outcome of the culturing of mammalian cells, in particular cells of the immune system.

Thus, the present invention provides a method for preparing a cell culture medium comprising a mixture of blood products from two or more donors, comprising the steps of:
a) providing at least a first blood product from a first donor;
b) measuring the concentration of at least one quality factor in the first blood product;
c) comparing the measured concentration of a quality factor to a concentration range predefined for the quality factor;
d) selecting the first blood product for the cell culture medium if the concentration measured for the quality factor is in the predefined range and optionally converting the first selected blood product into a first processed blood product or else unselecting the first blood product.

The invention further comprises a cell culture medium, comprising based on the volume of the cell culture medium:
CCL5 in a concentration of below 3 ng/ml;
Eotaxin in a concentration of below 500 pg/ml,
PDGF-88 and/or CXCL-10 in a concentration of below 100 pg/ml;
IL-10 in a concentration of below 200 pg/ml for;
IL-13 in a concentration of below 50 pg/ml for;
IL-1b, IL-2, IL-4, IL-5, IL-6, IL-7, IL-8, IL-9, IL12p70, IL-15, IL-17a, IL-21, basic FGF, EGF, IFNγ, GCSF, GM-CSF, MCP1, MIP1a, MIP1b, PDGF, IL-1RA, and/or TNFα in a concentration of below 20 pg/ml;
estradiol in a concentration of at least 65 pmol/l, preferably at least 75 pmol/l, more preferably at least 85 pmol/l;
cortisol in a concentration of at least 190 nmol/l, preferably at least 210 nmol/l, more preferably at least 220 nmol/l;
IGF-1 in a concentration of at least 80 µg/l, preferably at least 120 µg/l, more preferably at least 140 µg/l; and/or
SHBG in a concentration of below 31 nmol/l, preferably below 29 nmol/l.

Finally, the invention provides the use of the cell culture medium for culturing cells.

DETAILED DESCRIPTION OF THE INVENTION

The inventors have found that for cell culture immunotherapy much higher quality standards with regard to the cell culture medium have to be met. As shown in the examples, differences in the respective quality factors lead to significant changes in the outcome of lymphocyte suspension. In particular, with a medium in which the quality factors are in the predetermined ranges, growth, proliferation or expansion of immune cells lead to an increased proliferation rate, viability and activity of the cells. Identification of these quality factors allows the determination of an improved method for preparing a cell culture medium, in particular for cell populations for immunotherapy.

Thus, the present invention provides a method for preparing a cell culture medium comprising a mixture of blood products from two or more donors, comprising the steps of:
a) providing at least a first blood product from a first donor;
b) measuring the concentration of at least one quality factor in the first blood product;
c) comparing the measured concentration of a quality factor to a concentration range predefined for the quality factor;
d) selecting the first blood product for the cell culture medium if the concentration measured for the quality factor is in the predefined range and optionally converting the first selected blood product into a first processed blood product or else unselecting the first blood product.

The method according to the invention provides a cell culture medium with high quality that in combination with factors for lymphocyte expansion allows a strong proliferation of the cells and a high activity of the expanded lymphocytes. Moreover, the method ensures the provision of a consistent quality cell culture media for facilitating the in vitro expansion of lymphocytes such as T-cells.

As used herein "cell culture medium" or "growth medium" is a liquid or gel designed to support the growth of animal or plant cells. Growth media can vary in pH, glucose concentration, growth factors and the presence of other nutrients. There are two classes of cell culture media: blood product based media and synthetic media.

According to the invention "blood product based media" contain at least one blood product.

As used herein a "synthetic medium" is a chemically define medium. Such a medium does not contain any nature derived broth such as blood products. Instead, all components are added to the medium in defined concentrations.

As used herein "blood product" refers to whole blood of a mammal or subsets of whole blood, in particular plasma, serum or further subsets of plasma and serum.

As used herein "processed blood product" include plasma, serum and subset thereof.

"Plasma", as used herein refers to the blood plasma of mammals. It is a pale white sometimes yellow liquid component of blood that normally holds the blood cells in whole blood in suspension. Plasma is mostly water and contains dissolved proteins, glucose, clotting factors, electrolytes, hormones and carbon dioxide. Blood plasma can be prepared from blood, for example by centrifugation of fresh blood containing an anticoagulant in which the blood cells fall to the bottom of the centrifugation tube. The supernatant is then the blood plasma.

"Serum" as used herein is a blood plasma without coagulation factors.

"Coagulation factor" as used herein also referred to as "clotting factor" includes a variety of proteins, such as fibrinogen, prothrombin or factor VII.

"Subset of whole blood" as used herein refer to a solution or a suspension derived from whole blood comprising a part of the components of whole blood. Plasma and serum are subsets of whole blood.

"Donor" as used herein refers to a mammal, in particular a human, from which a blood product is obtained. The donation may be whole blood (WB) or specific components of whole blood retrieved by apheresis.

"Apheresis" as used herein is a medical technology in which blood of a donor is passed through an apparatus that separates out one particular constituent and returns the remainder to the circulation. For example, plasmapheresis leads to a collection of only blood plasma; all other components are returned to the donor.

As used herein, "obtaining a blood product" from a donor refers to the act of retrieving blood from a donor, in particular by taking the blood directly from the vein of the donor.

"Cytokines", as used herein, are a broad and loose category of small proteins (~5-20 kDa) that are important in cell signaling. They are released by cells and affect the behavior of other cells. Cytokines can also be involved in autocrine signaling. Cytokines include chemokines, interferons, interleukins, lymphokines, tumour necrosis factor and growth factors.

"Clinically relevant lymphocytes" are also referred to as antigen-edited lymphocytes. The term clinically relevant is also used for subgroups of lymphocytes. Particularly preferred clinically relevant lymphocytes are clinically relevant T-cells or antigen-edited T-cells.

"Clinically relevant antigens" according to the invention are antigens involved in a disease. Accordingly, clinically relevant antigens can be tumor-associated antigens TAA, pathogen associated antigens (PAA) or autoantigens. Tumor-reactive lymphocytes are specific for and interact with TAAs. Infectious disease reactive lymphocytes are specific for and interact with PAAs and autoimmune disease reactive lymphocytes are specific for and interact with autoantigens.

According to the invention an "antigen" (Ag) is any structural substance which serves as a target for the receptors of an adaptive immune response, TCR or antibody, respectively. Antigens are in particular proteins, polysaccharides, lipids and substructures thereof such as peptides. Lipids and nucleic acids are in particular antigenic when combined with proteins or polysaccharides.

Providing a blood product from a donor or multiple donors does not include the process of obtaining the blood product.

According to the invention a quality factor can be any component that may be found in the blood and the concentration of which has an impact on the growth and properties of a highly sensitive cell line such as cells of the immune system and stem cells.

Cells of the immune system include, but are not limited to, B-cells, T-cells, NK cells. monocytes, dendritic cells, granulocytes and platelets.

Blood derived media have the disadvantage that there is a variance of the ingredients due to fluctuations from one donor to the next.

As used herein "pathogen related factors" are factors that identify the presence of pathogens in the blood. Commonly tested pathogens are for example anti-*Trypanosoma cruzi*, hepatitis B virus (HBV), hepatitis C virus (HCV), parvo virus, varicella-zoster virus, hepatitis E virus (HEV) and human immunodeficiency viruses types 1 and 2 (HIV-1, HIV-2). The testing for pathogen related factors minimizes the risk of using an infected blood product. Preferably, a quality factor is not a pathogen related factor.

Human blood donors comprise voluntary donors and professional monitored donors. Both donors have to be healthy individuals. Furthermore, human blood donors have to fulfill certain criteria such as age, body weight and diet. Professional monitored blood donors are entered into a registry. In the registry a variety of data about the donor and the provided blood samples is recorded.

Providing a first blood product includes in particular the transfer of the blood product into a blood bag kit, bag, container, vessel or multiwell plate. According to one embodiment a first blood product from a first donor is transferred in a blood bag kit.

According to one embodiment a first blood product from the first donor is transferred into a multiwell plate. A multiwell plate is in particular a 24-well plate, a 48-well plate, a 96-well plate or a 192-well plate. A multiwell plate is a plate with a multiplicity of wells. The number of wells is not limited.

For measuring the concentration of a quality factor a variety of methods are known in the art. According to one embodiment of the present invention the quality factor is measured by a method selected from nephelometry, turbidimetry and ELISA. A nephelometer is an instrument for measuring the concentration of suspended particles in a liquid or gas colloid.

Nephelometry (and turbidometry) are defined in Euronorm EN 27027 (identical to the German DIN-Norm the ISO Norm 7027. A nephelometer measures suspended particulates by employing a light beam and a light detector set to one side of the source beam. In nephelometry to the sample of the blood product antibodies specific for the quality factors are added. Interaction of the antibodies with the quality factors then leads to a participation causing a side scattering of the light. Thus, either the increase or decrease can be qualified. In nephelometry the increase of side-scattered light is measured. In turbidimetry the decrease of forward-scattered light is measured. The results of the nephelometric measurement are given as nephelometric turbidity units (NTU) and by calibration with an NTU-curve with defined concentration values of a quality factor are related to a concentration value of the quality factor.

Enzyme-linked immunosorbent assay (ELISA) is a solid-phase assay for determining the presence and quality of antigens, in particular a sandwich ELISA can be used. The presence of pathogen related factors is in particular determined by PCR-based methods.

Comparing the measured concentration of a quality factor to concentration range predefined for the quality factor means that a read out obtained from the measurement for a specific quality factor is taken and it is checked whether the value of the quality factor is in the range of the predetermined range. The testing may be done automatically by the testing apparatus or an apparatus connected to the testing apparatus. Alternatively, the comparison can be performed manually by a person carrying out measurement.

A preferred quality factor according to the invention is a cytokine or a number of cytokines. The quality factor can be a group of cytokines. Moreover, the quality factor can be all cytokines. As shown in the examples it was determined for a variety of cytokines that the presence of these cytokines outside the predefined range that means above certain threshold strongly decreases the quality of the medium with respect to its ability to growth and/or expand cells of the immune system or stem cells. In particular it is not possible to obtain expanded lymphocytes in a quality for immunotherapy.

Thus, according to one embodiment a quality factor is a cytokine. However other components have been found to strongly influence the quality of the expansion medium with regard to the ability to grow, in particular expand, cells of the immune system.

Interestingly, a medium with a quality factor outside of the predefined range, i.e. non-selected medium can still be useful for growing cells for recombinant protein expression. Further quality factors that have been identified are estradiol, cortisol, sex hormone-binding globulin (SHBG), insulin and insulin-like growth factor 1 (IGF-1).

However, further quality factors may not be mentioned specifically but also influence to quality of the medium with regard to growth and expansion of lymphocytes while not necessarily influencing growth of standard cell lines. According to one embodiment of the present invention at least one quality factor is selected from the group consisting of estradiol, cortisol, SHBG, insulin and IGF-1.

There are a variety of cytokines, the presence of which outside the predefined range leads to an unselecting of the blood product. One quality factor is CCL5, also known as RANTES. The predefined range for CCL5 is below 5, in particular below 3 ng/ml.

All concentration values are as defined by Nephelometrie according to ISO 7027. Accordingly, the upper threshold is 5 ng/ml, in particular 3 ng/ml; all concentrations defined for the quality factors are based on the volume of the blood product.

A further quality factor is the cytokine Eotaxin. The predefined range of Eotaxin is below 800 pg/ml, in particular 500 pg/ml. Another quality factor is PDGF-88. The predefined range of PDGF-88 is below 150 pg/ml, in particular below 100 pg/ml or. A further quality factor is CXCL-10. The predefined range of CXCL-10 is below 150 pg/ml, in particular below 100 pg/ml. A further quality factor is the cytokine IL-10. The predefined range for IL-10 is below 200 pg/ml. Another quality factor is the cytokine IL-13. The predefined range of IL-13 is below 80 pg/ml, in particular below 50 pg/ml. A further quality factor is IL-1b. The predefined range of IL-1b is below 30 pg/ml, in particular below 20 pg/ml. A further quality factor is IL-2. Another quality factor is IL-4. IL-5 is another quality factor. IL-7 is another quality factor. Also IL-8 is another quality factor. A further quality factor is IL-9. According to the invention also IL-12p70 is a quality factor. Another quality factor is IL-15. One quality factor according to the invention is IL-17a. IL-21 is another quality factor. A further quality factor is basic FGF. Epidermal growth factor (EGF) is a further quality factor. Another quality factor is interferon gamma (IFNγ). Granulocyte-colony stimulating factor (GCSF) is another quality factor according to the invention. Granulocyte-macrophage colony-stimulating factor (GM-CSF) is a further quality factor according to the invention. Moreover, MCP1 was determined as a quality factor. Another quality factor determined is MIP1a. Also MIP1b. A further quality factor is PDGF. Moreover, IL-1RA is another quality factor and the tumor necrosis factor α (TNFα) is another quality factor. All these factors are known cytokines that may be present in the human blood.

For the factors IL-1b IL-2, IL-4, IL-5, IL-6, IL-7, IL-8, IL-9, IL12p70, IL-15, IL-17a, IL-21, basic FGF, EGF, IFNγ, GCSF, GM-CSF, MCP1, MIP1a, MIP1b, PDGF, Il1RA, and TNFα is below 30 pg/ml, in particular below 20 pg/ml.

All the cytokines listed above were found to influence the culturing, in particular expansion of lymphocytes, immune cells or also stem cells. Accordingly these cytokines are only allowed to a certain upper threshold. Other quality factors are necessary to be included in the blood product at least to a certain extent.

According to one embodiment the quality factor is estradiol. Estradiol should be in blood product with a concentration of at least 65 pmol/l. A preferred concentration for estradiol is at least 75 pmol/l. More preferably, the concentration of estradiol is at least 85 pmol/l.

According to one embodiment of the invention the quality factor is cortisol. The predefined range for cortisol is at least 190 nmol/l, preferably at least 210 nmol/l, more preferably at least 220 nmol/l.

According to one embodiment of the invention the quality factor is insulin-like growth factor 1 (IGF-1). According the one embodiment the predefined range for IGF-1 is at least 100 μg/l, preferably at least 130 μg/l, more preferably at least 140 μg/l.

There is a variety of further parameters that cell culture medium according to the invention should fulfill. In particular, standard culture factors being present in predefined ranges. Accordingly, the method further comprises measuring standard culture factors and comparing them to predefined ranges Examples of standard culture factors are: proteins, glucose, non-protein nitrogen, urea nitrogen, amino acid nitrogen, creatinine, creatine, urea, total lipids, triglyceride, cholesterine, lipids, esterified components, phospholipids, fatty acids, organic acids, pyruvate, citrate, ketones.

The predefined range based on the total volume of the cell culture medium is for proteins 60.080.0 g/l; for glucose 4.5 to 5.5 mmol/l, for non-protein nitrogen 15 to 30 mmol/l, for urea nitrogen 3.5 to 7.0 mmol/l, for amino acid nitrogen 3.0 to 5.0 mmol/l; for creatinine 70.0 to 140.0 pmol/l; for creatine 25.0 to 70.0 pmol/l; for urea 3.0 to 5.0 pmol/l; for total lipids 4.5 to 8.5 g/l, for triglycerides 0.6 to 2.4 mmol/l, for cholesterine 4.0 to 6.5 mmol/l, lipids in a concentration of 0.3 to 0.4 mmol/l, for esterified components 0.7 to 0.8 mmol/l, for phospholipids 2.0 to 3.0 mmol/l, for fatty acids 0.3 to 0.9 mmol/l; for organic acids 4.0 to 6.0 mmol/l, for pyruvate 0.1 to 0.2 mmol/l, for citrate 0.1 to 0.2 mmol/l, and for ketones in a concentration of 0.3 to 0.5 mmol/l.

According to one embodiment of the invention the steps are to be performed with more than one blood product and the selected blood product or processed blood products are combined to form a culture medium. From one donor only about 200 to 500 ml blood product can be obtained at once. Accordingly, for the cultivation of cells several blood products of several donors have to be combined. For the preparation of the cell culture medium only selected blood products are used.

If in an unselected sample the one or more quality factors in a blood product exceed the upper limit—if applicable—by less than 30%, more preferably by less than 20%, most preferably by less than 10% of the value of the upper limit of the quality factor, the blood product is a temporary unselected blood product. Moreover, if in an unselected sample the one or more quality factors in a blood product exceed the lower limit—if applicable—by less than 30%, more preferably by less than 20%, most preferably by less than 10% of the value of the upper limit of the quality factor, the blood product is a temporary unselected blood product. A temporary unselected blood product may become a selected blood product if it is possible to mix the temporary unselected blood product with at least one selected blood product to obtain a blended blood product with the quality factors in the defined ranges. Else the temporary unselected blood product becomes an unselected blood product.

It is also possible to determine the concentration of the at least one quality factor in a mixture of products. Thus, the present invention further provides a method for preparing a cell culture medium comprising a mixture of blood products from two or more donors comprising the steps of
a) providing a at least a first mixture of blood products from two or more donors;
b) measuring the concentration of at least one quality factor in the first mixture;
c) comparing the measured concentration of a quality factor to a concentration range predefined for the quality factor;
d) selecting the first mixture for the cell culture medium if the concentration measured for the quality factor is in predefined range or else unselecting the first mixture.

Also, it is preferred to measure the concentration of the quality factors directly in the blood products before adding the blood product to the mixture to form a culture medium. It is also possible to screen various mixtures of blood products and verify if these fulfill the requirements as determined by the quality factors.

The blood product can be converted into a processed blood product after selection and before addition to the final product, i.e. the cell culture medium. Processing the blood product means rendering one type of blood product into another type of blood product. For example the blood product measured and selected is whole blood which is then further converted into plasma. Alternatively, the measured and selected blood product is whole blood and the processed blood product is serum. Another option is that the selected blood product is plasma and the processed blood product is serum. Another option is that the selected blood product is plasma and the processed blood product is subset of serum. Also the selected blood product can be serum and the processed blood product is a subset of serum.

Preferably the blood product that is provided is plasma. Plasma is frequently used for cultivation of for example cells of the immune system. Moreover, plasma can be easily retrieved by plasmapheresis from the donor. Accordingly also the processed blood product is plasma. Using plasma has the advantage that no further process step is necessary. Thus, saving the processing step.

Preferably two or more quality factors are tested, for example 2, 3, 4, 5, 6, 7, 8, 9, 10, 11, 12, 13, 14, 15, 16, 17, 18, 19, 20 quality factors are tested. Testing more quality factors increases the chance of obtaining a final cell culture medium that indeed fulfills the higher quality standards for culturing and expanding highly active lymphocytes. However testing a large amount of factors in one sample also leads to an increased complexity of the process. Thus preferably less than 15, less than 12, less than 10, less than 8, less than 6 quality factors are tested.

According to one embodiment of the invention the number of quality factors tested is in the range from 2 to 6, preferably 3 to 5, preferably 4. It was found that a certain subset of the known quality factors are sufficient to find a high likelihood that the cell culture medium is a cell medium eligible for expansion of lymphocytes or cultivation of stem cells. Quality factors that are shown to provide an indication that the whole sample is a high quality sample are SHBG, IGF-1, CCL5 and IL-6. Thus, preferably the quality factor is SHBG. Also preferred is IGF-1 as quality factor. Likewise CCL5 is a preferred quality factor. IL-6 is also a preferred quality factor. According to one embodiment of the invention all quality factors are tested are SHBG, IGF-1, CCL5 and IL-6.

The test for a quality factor may also be used for the selection of suitable donors, in particular professional monitored donors. Professional monitored donors regularly donate blood product donations and are recorded in a registry.

With the method according to the invention a blood donor can be identified as appropriate for donation of high quality blood products. Accordingly the method according to the invention provides a further selection step on the level of the donor.

According to one embodiment the method comprises a donor selection:
a) providing a blood product from the donor;
b) measuring the concentration of at least one quality factor in the blood product of a first donor;
c) comparing the measured concentration a quality factor to the concentration range predefined for the quality factor;
d) selecting the donor for plasma or serum donation if the concentration value for the plasma pool if the concentration measured for the quality factor is in predefined range or else unselecting the first donor.

Donors that are unselected are removed from the registry for high quality blood product.

The present invention also relates to a cell culture medium comprising, based on the volume of the cell culture medium:
CCL5 in a concentration of below 3 ng/ml;
Eotaxin in a concentration of below 500 pg/ml,
PDGF-88 and/or CXCL-10 in a concentration of below 100 pg/ml;

IL-10 in a concentration of below 200 pg/ml for;
IL-13 in a concentration of below 50 pg/ml for;
IL-1b, IL-2, IL-4, IL-5, IL-6, IL-7, IL-8, IL-9, IL12p70, IL-15, IL-17a, IL-21, basic FGF, EGF, IFNγ, GCSF, GM-CSF, MCP1, MIP1a, MIP1b, PDGF, Il1RA, and/or TNFα in a concentration of below 20 pg/ml;
estradiol in a concentration of at least 65 pmol/l, preferably at least 75 pmol/l, more preferably at least 85 pmol/l;
cortisol in a concentration of at least 190 nmol/l, preferably at least 210 nmol/l, more preferably at least 220 nmol/l;
IGF-1 in a concentration of at least 100 μg/l, preferably at least 130 μg/l, more preferably at least 140 μg/l; and/or
SHBG in a concentration of below 31 nmol/l, preferably below 29 nmol/l.

The medium provides nutritions necessary for T-cell culturing and expansion in a controlled and artificial environment enabling stable and reproducible results.

The cell culture medium is preferably a medium obtained by the method of preparation according to the invention. According to one embodiment the cell culture medium comprises at least one blood product, in particular plasma and/or serum. More preferably the blood product is serum. According to a further embodiment the cell culture medium comprises blood products from two or more donors. Preferably the blood products from two or more donors are selected from serum and/or plasma. More preferably, the products from two or more donors are serum. According to an alternative embodiment the cell culture medium is a synthetic medium.

There is a variety of further parameters that the cell culture medium according to the invention should fulfill. In particular, standard culture factore being present in predefined ranges. Examples of standard culture factors are: proteins, glucose, non-protein nitrogen, urea nitrogen, amino acid nitrogen, creatinine, creatine, urea, total lipids, triglyceride, cholesterine, lipids, esterified components, phospholipids, fatty acids, organic acids, pyruvate, citrate, ketones.

Accordingly, the cell culture medium of the invention further comprises
proteins in a concentration of 60.080.0 g/l;
glucose in a concentration of 4.5 to 5.5 mmol/l;
non-protein nitrogen in a concentration of 15 to 30 mmol/l;
urea nitrogen in a concentration of 3.5 to 7.0 mmol/l;
amino acid nitrogen in a concentration of 3.0 to 5.0 mmol/l;
creatinine in a concentration of 70.0 to 140.0 μmol/l;
creatine in a concentration of 25.0 to 70.0 μmol/l;
urea in a concentration of 3.0 to 5.0 μmol/l;
total lipids in a concentration of 4.5 to 8.5 g/l;
triglycerides in a concentration of 0.6 to 2.4 mmol/l;
cholesterine in a concentration of 4.0 to 6.5 mmol/l;
lipids in a concentration of 0.3 to 0.4 mmol/l;
esterified components in a concentration of 0.7 to 0.8 mmol/l;
phospholipids in a concentration of 2.0 to 3.0 mmol/l;
fatty acids in a concentration of 0.3 to 0.9 mmol/l;
organic acids in a concentration of 4.0 to 6.0 mmol/l;
pyruvate in a concentration of 0.1 to 0.2 mmol/l;
citrate in a concentration of 0.1 to 0.2 mmol/l; and/or
ketones in a concentration of 0.3 to 0.5 mmol/l.

Preferably the cell culture medium fulfills all of the parameters mentioned above. According to one embodiment the cell culture medium comprises either one of SHBG in a concentration of below 29 nmol/l;
IGF-1 in a concentration of at least 100 μg/l,
IL-6 in a concentration of below 20 pg/ml; and
CCL5 in a concentration of below 3 ng/ml.

According to a further embodiment the cell culture medium comprises
SHBG in a concentration of below 29 nmol/l;
IGF-1 in a concentration of at least 100 μg/l,
IL-6 in a concentration of below 20 pg/ml; and
CCL5 in a concentration of below 3 ng/ml.

The cell culture medium according to the invention may consist of a mixture of blood products. Preferably the cell culture medium comprises in addition to the mixture of blood products further components. According to a preferred embodiment the further components are selected from water, NaCl, PBS, DTT, TCEP, or 2-mercaptoethanol.

The cell culture medium according to the invention is suitable for culturing a variety of different cells. Thus, the invention further provides the use of the cell culture medium for culturing cells. A major advantage is that besides the culturing of a immortal cell line also cells obtained from a patient, in particular cells of the immune system or stem cells, may be successfully cultured.

With a medium according to the invention, in particular a medium obtained with a method according to the invention, much higher expansion rates of lymphocytes are found. "Expansion" or "clonal expansion" as used herein means production of daughter cells derived originally from a single cell. In a clonal expansion of lymphocytes, all progenies shared the same antigen specificity.

Moreover, with the culture medium according to the invention in cell culture an increased total number of cells can be obtained. In particular, an increased number of total expanded daughter cells of lymphocytes with the same antigen specificity can be obtained.

Thus, according to one embodiment of the use the cells are cells of the immune system, in particular lymphocytes. Preferably, the lymphocytes are obtained from the patient. According to one embodiment the lymphocytes are grown, proliferated and/or expanded in the cell culture medium.

According to one embodiment the culture medium is used in the expansion of T-cells derived from tumor. Preferably the expansion involves the use of a cytokine cocktail of IL-2, IL-15 and IL-21. According to the invention the composition of IL-2, IL-15 and IL-21 also referred to as "the cytokine cocktail".

As used herein, "interleukin 2" or "IL-2" refers to human IL-2 and functional equivalents thereof. As used herein, "interleukin 15" or "IL-15" refer to human IL-15 and functional equivalents thereof. As used herein, "interleukin 21" or "IL-21" refer to human IL-21 and functional equivalents thereof.

The cell culture medium according to the invention, preferably a medium obtained by the method according to the invention, is in particular suitable for the expansion of lymphocytes in combination with a cytokine mixture of IL-2, IL-15 and/or IL-21. Preferably in combination with this mixture of cytokines the cell culture medium according to the invention provides an increased growth rate, an increased total number of expanded cells but also an improved profile of the cells. In particular the maturation and differentiation defined by the CD45RA/CCR7 phenotype is improved. Finally it is found that an expansion of lymphocytes with a mixture of cytokines IL-2, IL-15 and IL-21 leads to an increased viability of clinically relevant lymphocytes, in particular T-cells.

In active cellular immunotherapy the increased growth and expansion rate decreases the time from obtaining the lymphocyte sample from the patient to the time of reintroducing the standard lymphocytes into the patient. The increased viability of the (clinically relevant) lymphocytes leads to an increased therapeutical effect of the active immunotherapy product.

Many modifications and other embodiments of the invention set forth herein will come to mind to the one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

EXAMPLES

Example 1—Expansion of Lymphocytes in Different Cell Culture Media

Aphaeresis was performed on a healthy donor primed with NY-ESO-1. After separation of the blood components, the product containing the leucocytes is separated from the rest.

Cells were suspended in medium M1 with 1000 U/ml IL-2, 10 ng/ml IL-15 and 10 ng/ml IL-21. The medium in addition contained 10 μmol NY-ESO-1 peptide. The cells expanded well reaching a concentration of $10^6$/ml after 4 days.

In parallel lymphocytes were expanded in medium M2 according to the same protocol. No significant expansion of lymphocytes was detected.

Example 2—Analysis of the Composition Cell Culture Media

Standard tests did not reveal any difference between the cell culture media. Using nephelometry and antibodies against the substances listed as components in Table 1 the media M1 and M2 were analysed in more detail

TABLE 1

| Component | Unit | M1 | M2 |
|---|---|---|---|
| Triglyceride | mmol/l | 1.1 | 0.99 |
| Colesterol | mmol/l | 4.1 | 2.8 |
| HDL-colesterol | mmol/l | 1.1 | 0.9 |
| LDL-colesterol | mmol/l | 2.5 | 1.5 |
| Estradiol | pmol/l | 86 | 57 |
| T3 | pmol/l | 11 | 12 |
| T4 | pmol/l | 4.4 | 4.5 |
| Cortisol | nmol/ | 231 | 179 |
| Testosteron | nmol/l | 12 | 12 |
| SHGB | nmol/l | 26 | 31 |
| Insulin | mIE/l | 7.2 | 5.0 |
| IGF-1 | μg/l | 157 | 86 |
| S-GH | μg/l | 0.3 | 0.3 |

Example 3—Analysis of the Plasma of Different Donors

According to the results from the analysis of the cell culture media, plasma samples from different professionally monitored donors were obtained and analyzed with respect to concentration of estradiol, cortisol, insulin, and IGF-1. The results are presented in Table 2.

TABLE 2

| Component | Unit | P1 | P2 | P3 | P4 | P5 |
|---|---|---|---|---|---|---|
| Estradiol | pmol/l | 53 | 56 | 58 | 88 | 87 |
| Cortisol | nmol/ | 231 | 233 | 177 | 235 | 230 |
| Insulin | mIE/l | 7.2 | 4.9 | 7.3 | 7.4 | 7.5 |
| IGF-1 | μg/l | 84 | 154 | 158 | 157 | 156 |

According, to the method of the invention the plasma samples P1 to P4 are unselected. Plasma sample P5 is selected for lymphocyte culture.

Example 4—Analysis of the Plasma of Different Donors

To confirm the plasma selection the plasma samples P1 to P5 were then prepared for cell culture. Lymphocytes obtained from peripheral blood of a healthy donor primed with NY-ESO-1 were cultured according to the above described protocol. Expansion in cell culture medium from P5 was comparable to the expansion in medium M1 (see Example 1).

The invention claimed is:

1. A method for preparing a lymphocyte culture medium comprising a mixture of blood products from two or more donors, comprising the steps of:
   a) providing at least a first blood product from a first donor, comprising transferring the blood product into a container selected from the group consisting of a blood bag kit, a bag, a multi-well plate and a vessel;
   b) measuring the concentration of one or more quality factors in the first blood product with a method selected from the group consisting of nephelometry, turbidimetry and enzyme linked immunosorbent assay (ELISA), wherein the one or more quality factors are selected from the group consisting of estradiol, cortisol, insulin-like growth factor 1 (IGF-1), insulin, and sex hormone binding globulin (SHBG);
   c) comparing the measured concentration of the one or more quality factors to a concentration range predefined for the one or more quality factors, wherein the predefined concentration range, based on the volume of the blood product, is:
   at least 65 pmol/l for estradiol;
   at least 190 nmol/l for cortisol;
   at least 100 μg/l for IGF-1; and/or
   below 31 nmol/l for SHBG;
   d) selecting the first blood product for the lymphocyte culture medium if the concentration measured for at least one of the quality factors is in the predefined range;
   e) converting the first selected blood product into a first processed blood product selected from plasma and serum or else unselecting the first blood product, wherein the steps a) to e) are performed with more than one blood product from different donors and the processed blood products are combined to form the culture medium;
   f) adding one or more of interleukin 2 (IL-2), IL-15 and IL-21 to the culture medium; and g) adding one or more of water, NaCl, phosphate buffered saline (PBS), dithiothreitol (DTT), tris(2-carboxyethyl) phosphine (TCEP) and beta-mercaptoethanol to the culture medium.

2. The method according to claim 1, wherein the at least first blood product from two or more donors is selected from whole blood, plasma, serum or subsets thereof.

3. The method according to claim 1, wherein two or more quality factors are tested.

4. The method according claim 1, wherein the predefined concentration range, based on the volume of the blood product, is:
- at least 85 pmol/l for estradiol;
- at least 220 nmol/l for cortisol;
- at least 140 µg/l for IGF-1; and
- below 29 nmol/l for SHBG.

\* \* \* \* \*